United States Patent [19]

Hayashi et al.

[11] Patent Number: 5,306,413
[45] Date of Patent: Apr. 26, 1994

[54] ASSAY APPARATUS AND ASSAY METHOD

[75] Inventors: Ryuzo Hayashi, Higashiosaka; Yukie Inoue, Tsuzuki; Akio Kariyone, Kyoto, all of Japan

[73] Assignee: Kanzaki Paper Manufacturing Co., Ltd., Tokyo, Japan

[21] Appl. No.: 37,421

[22] Filed: Mar. 26, 1993

[30] Foreign Application Priority Data

Mar. 31, 1992 [JP] Japan .................. 4-077257

[51] Int. Cl.$^5$ .................. G01N 27/26
[52] U.S. Cl. .................. 204/403; 204/409; 435/291; 435/817
[58] Field of Search .............. 204/403, 409; 435/291, 435/817

[56] References Cited

U.S. PATENT DOCUMENTS

| | | | |
|---|---|---|---|
| 4,525,265 | 6/1985 | Abe et al. | 204/403 |
| 5,037,737 | 8/1991 | Liffmann et al. | 204/403 |
| 5,081,015 | 1/1992 | Hayashi et al. | 204/403 |
| 5,206,145 | 4/1993 | Cattell | 204/403 |
| 5,225,321 | 7/1993 | Hayashi et al. | 204/403 |

FOREIGN PATENT DOCUMENTS 0310824  4/1989  European Pat. Off. .

*Primary Examiner*—John Niebling
*Assistant Examiner*—Bruce F. Bell
*Attorney, Agent, or Firm*—Larson and Taylor

[57] ABSTRACT

The present invention relates to a simple and yet multi-functional system for assay employing immobilized enzymes.

4 Claims, 5 Drawing Sheets

ASSAY APPARATUS AND ASSAY METHOD

FIELD OF THE INVENTION

The present invention relates to a simple and yet multifunctional system for assay employing immobilized enzymes.

BACKGROUND OF THE INVENTION

The immobilized enzyme technology is used widely in such fields as food production, production of fine chemicals and solution of environmental problems by means of bioreactors. Said technology is also being used in the area of analytical chemistry, where the high substrate specificity, high reaction rate and high sensitivity characteristics of enzymes are utilized. Analytical devices utilizing immobilized enzymes are generally known as biosensors and now are being studied widely.

Biosensors can be classified, by the detection technique employed therein, into electrode, field effect transistor, photodetector, thermal detector and other types. Among these, the electrode-type biosensors are simple in construction and can be provided with added specificity by selection of the electrode as well as the enzyme species used. Furthermore, unlike field effect transistor-type biosensors, they are scarcely influenced by pH and, unlike photodetection-type biosensors, they are virtually indifferent to the color or turbidity of samples. Accordingly, various apparatus or devices based on biosensors of the electrode type in particular have been developed.

Biosensors using electrodes are further classifiable into two major types, namely amperometric sensors in which an oxygen electrode, a hydrogen peroxide electrode or the like is used and potentiometric sensors which employ an ion selective electrode such as a pH electrode or an ammonia electrode. Amperometric sensors are used more frequently since they give a linear relationship between substance concentration and output electric current value, which facilitates data processing and make it possible to construct high-accuracy and high-sensitivity apparatus with a simple structure.

Since the measurement technique using biosensors is advantageous not only in accuracy and sensitivity as mentioned above but also in the ease and simplicity of operation and data processing, the range of application of this technique is expanding.

However, most of the biosensors available today employ an oxidase and measure the concentration of oxygen which decreases or the concentration of hydrogen peroxide which increases. In other words, with these biosensors, the targets of measurement are limited to substances of the oxidase employed. Therefore, assay systems employing a variety of other enzymes such as hydrolase, isomerase, dehydrogenase, etc., each in immobilized form, together with an immobilized oxidase are also in use. The use of these immobilized enzymes is advantageous in that the range of targets of assay is extended, the measurement sensitivity can be improved and the rate of reaction can be increased, for instance.

Among such assay systems, the assay system for lactic acid and pyruvic acid is attracting particular attention because of its importance in, inter alia, fermentation control and clinical diagnosis. A typical example can be found in alcohol fermentation. In alcohol fermentation, it is important to know both the concentration of lactic acid and that of pyruvic acid as indices of whether the metabolic system of the yeast is working normally or not. This is particularly important in the process for brewing sake.

As known examples of the assay system, the following may be mentioned.

(1) The method comprising immobilizing L-lactate oxidase on a carrier and assaying lactic acid based on the quantity of hydrogen peroxide formed.

(2) The method comprising immobilizing L-lactate dehydrogenase on a carrier, reducing pyruvic acid in the presence of NADH and assaying pyruvic acid based on the decrease in absorbance at 340 nm.

(3) The method comprising contacting pyruvic acid with pyruvate oxidase in the presence of $FAD^+$, TPP (thiamine pyrophosphonate) and $Mg^{2+}$ to form acetylphosphate and assaying pyruvic acid based on the change in quantity of hydrogen peroxide or oxygen.

(4) The method comprising co-immobilizing L-lactate oxidase and L-lactate dehydrogenase, bringing a substrate into contact with both immobilized enzymes simultaneously to thereby reduce the substrate which has been oxidized by oxidase-catalyzed reaction by means of the dehydrogenase and re-oxidize the thus-reduced substrate by oxidase-catalyzed reaction in repetition and assaying either pyruvic acid or lactic acid or both together, with high sensitivity. This assay method utilizes the principle of enzyme cycling, i.e., the phenomenon that a larger number of molecules of oxygen than molecules of the substrate are converted to hydrogen peroxide (Japanese Examined Patent Publication No. 3-65492).

The methods (1) and (2) mentioned above can assay only either lactic acid or pyruvic acid. In cases where it is necessary to assay both, lactic acid and pyruvic acid must be assayed separately. This is because, by the L-lactate oxidase lactic acid is oxidised to pyruvic acid in the method (1), hydrogen peroxide which can be measured with high sensitivity at the electrode is formed. And in the method (2), by the L-lactate dehydrogenase pyruvic acid is reduced, NADH, which is to be measured spectrophotemetrically, is decreased. Therefore if one tries to assay both of them simultaneously he cannot but fail because of the impossibility of precisely assaying both owing to the above difference in detection method.

The method (3) mentioned above has drawbacks that two coenzymes are required and pyruvate oxidase is not stable.

The disadvantage of the above cycling system (4) employing an enzyme combination is that once the enzymatic reaction has started, the oxidized form and the reduced form of the substrate for the dehydrogenase are both involved in the reaction. More specifically, when L-lactate dehydrogenase and L-lactate oxidase are immobilized and cycling is performed, pyruvic acid in the sample is first converted to L-lactic acid and at the same time L-lactic acid is converted to pyruvic acid by the oxidase-catalyzed reaction, if NADH (reduced-form nicotinamide adenine dinucleotide) coexists in the system. If NADH is present in a sufficient amount and the amount of dissolved oxygen is also sufficient, that cycle is repeated and consequently the hydrogen peroxide formed upon oxidation of lactic acid is accumulated. Therefore, when the decrease in the concentration of oxygen or the increase in the concentration of hydrogen peroxide is detected electrochemically, an improved sensitivity can be obtained as compared with the case where no cycling is performed. However, if the sample contains L-lactic acid from the beginning, this cannot be distinguished from pyruvic acid. In other words, the quantity of pyruvic acid cannot be determined exactly.

The prior art assay methods using immobilized enzymes thus encounter the problems mentioned above. No effective apparatus have been disclosed as yet for reaction systems in which a dehydrogenase is utilized. This is particularly because the dehydrogenase-catalyzed oxidation of substrates in the presence of NAD+ can hardly proceed, hence it is a general practice to use an oxidase, and because the dehydrogenase-catalyzed oxidation of substrates produces NADH, which is not suited for high-sensitivity sensors.

The present invention relates to an assay apparatus and assay method in which a dehydrogenase in immobilized form and an oxidase in immobilized form are utilized. The object of the invention is to provide a multifunctional assay apparatus and assay method by which two components, namely an oxidized-form substrate (or a reduced-form coenzyme), and a reduced-form substrate of a dehydrogenase, can be simultaneously assayed.

DISCLOSURE OF THE INVENTION

Figure 1:
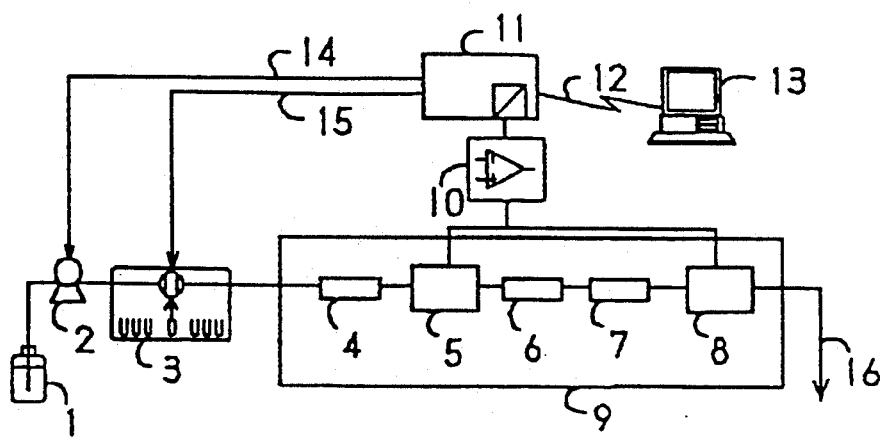
FIG. 1 is a schematic view showing an example of the assay apparatus of the invention which is used for the simultaneous assay of L-lactic acid and pyruvic acid using appropriate immobilized enzymes.

The invention provides an assay apparatus for assaying an oxidized-form substrate $B_{oxidized}$ (or a reduced-form coenzyme $A_{reduced}$), and a reduced-form substrate $B_{reduced}$ by means of:

a dehydrogenase which catalyzes the reaction between the reduced-form coenzyme $A_{reduced}$ and oxidized-form substrate $B_{oxidized}$ to form the corresponding oxidized-form coenzyme $A_{oxidized}$ and reduced-form substrate $B_{reduced}$; and an oxidase which catalyzes the oxidation of the reduced-form substrate $B_{reduced}$; which apparatus comprises:

(1) a first measuring part including the oxidase in immobilized form and a first electrode for detecting the change in the concentration of an electrochemically active substance, i.e., electrode-active substance, as resulting from the oxidase-catalyzed reaction and (2) a second measuring part including the dehydrogenase in immobilized form and the oxidase in immobilized from and a second electrode for detecting the change in the concentration of an electrochemically active substance, i.e., electrode-active substance, as resulting from the oxidase-catalyzed reaction.

The invention further discloses a preferred example of the assay apparatus mentioned above in which the first and second measuring parts are connected in series, with the second measuring part disposed downstreams of the first measuring part and in which, in the second measuring part, the immobilized dehydrogenase and immobilized oxidase are separately immobilized in respective reactors. The serial disposition of the first and second measuring parts is preferred since variations in the measurement conditions, such as pH, temperature and flow rate of buffer solution to cause measurement errors in that case, will not be occurred. This is because two objected substances are measured in one operation simultaneously.

The invention further discloses an example of the apparatus in which L-lactate dehydrogenase and L-lactate oxidase are used as the dehydrogenase and oxidase, respectively, as a preferred enzyme combination.

Furthermore, the invention provides a method of assaying an oxidized-form substrate $B_{oxidized}$ (or a reduced-form coenzyme $A_{reduced}$) and a reduced-form substrate $B_{reduced}$ by using:

a dehydrogenase catalyzing the reaction between the reduced-form coenzyme $A_{reduced}$ and oxidized-form substrate $B_{oxidized}$ to form the corresponding oxidized-form coenzyme $A_{oxidized}$ and reduced-form substrate $B_{reduced}$; and an oxidase catalyzing the oxidation of the reduced-form substrate $B_{reduced}$, which method comprises the steps of:

(i) bringing a sample, together with a buffer solution, into contact with the immobilized oxidase to thereby cause conversion of the reduced-form substrate $B_{reduced}$ in the sample to the oxidized-form substrate $B_{oxidized}$ and assaying the reduced-form substrate $B_{reduced}$ in the sample by detecting the change in the concentration of an electrochemically active substance as resulting from this conversion reaction, (ii) bringing the sample together with a buffer solution containing the reduced-form coenzyme $A_{reduced}$ (or the oxidized-form substrate $B_{oxidized}$), into contact with the immobilized dehydrogenase to thereby reduce the oxidized-form substrate $B_{oxidized}$ (or oxidize the reduced-form coenzyme $A_{reduced}$) to produce the reduced-form substrate $B_{reduced}$ and then bringing the sample into contact with an immobilized oxidase to thereby cause conversion of the thus-produced reduced-form substrate $B_{reduced}$ and the reduced-form substrate $B_{reduced}$ occurring in the sample from the beginning to oxidized-form substrate $B_{oxidized}$ and detecting the electrochemically active substance which varies in concentration upon the oxidase-catalyzed reaction to assay the total concentration of the reduced-form substrate $B_{reduced}$, and (iii) determining the concentration of the oxidized-form substrate $B_{oxidized}$ (or the reduced-form coenzyme $A_{reduced}$) by correcting the value obtained in step (ii) in the light of the value for the originally occurring reduced-form substrate $B_{reduced}$ as obtained in step (i).

When the reduced-formed coenzyme $A_{reduced}$ is added to the buffer solution, the above assay method can assay the oxidized-form substrate $B_{oxidized}$ and reduced-form substrate $B_{reduced}$. Similarly, when the buffer solution contains the oxidized-form substrate $B_{oxidized}$, the reduced-form coenzyme $A_{reduced}$ and reduced-form substrate $B_{reduced}$ can be assayed. The buffer solution has a preferable pH of about 6 to 9. As examples of the buffer solution, there may be mentioned phosphate buffer, Tris-hydrochloride buffer, and the like.

As the electrochemically active substance to be used in the practice of the invention, there may be mentioned hydrogen peroxide, oxygen, or mediators, such as p-benzoquinone, ferricyanides, tetrathiafulvalene, ferrocene and the like. The reduced-form coenzyme $A_{reduced}$ is, for example, NADH, NADPH, $FADH_2$, $FMNH_2$ or the like. The reduced-form substrate $B_{reduced}$ is, for example, ethanol, a natural L-amino acid, such as L-glutamic acid, glucose, L-lactic acid or galactose. The dehydrogenase includes, among others, alcohol dehydrogenase, L-amino acid dehydrogenase, L-glutamate dehydrogenase, glucose dehydrogenase, L-lactate dehydrogenase and galactose dehydrogenase.

As the oxidized-form coenzyme $A_{oxidized}$, oxidized-form substrate $B_{oxidized}$ and oxidase, there may be mentioned those respectively corresponding to the reduced-form coenzymes $A_{reduced}$, reduced-form substrates $B_{reduced}$ and dehydrogenases mentioned above as examples.

The measuring apparatus and measuring method of the present invention can be applied, for example, to the following systems:

(1) The system in which alcohol dehydrogenase and alcohol oxidase are used and by which acetaldehyde and ethanol, or ethanol and NADH or NADPH are assayed (pH of the buffer=about 7 to about 9);

(2) The system in which an L-amino acid dehydrogenase and an L-amino acid oxidase are used and by which the L-amino acid and the corresponding 2-keto acid, or the L-amino acid and NADH are assayed. (pH of the buffer=about 7 to about 8);

(3) The system in which L-glutamate dehydrogenase and L-glutamate oxidase are used and by which 2-ketoglutaric acid and L-glutamic acid, or L-glutamic acid and NADH or NADPH (reduced-form nicotinamide adenine dinucleotide phosphate) are assayed (pH of the buffer=about 6 to about 9);

(4) The system in which glucose dehydrogenase and glucose oxidase are used and by which glucose and glucono-δ-lactone, or glucose and NADPH are assayed (pH of the buffer=about 7 to about 9);

(5) The system in which L-lactate dehydrogenase and L-lactate oxidase are used and by which L-lactic acid and pyruvic acid, or L-lactic acid and NADH are assayed (pH of the buffer=about 7 to about 8); and (6) The system in which galactose dehydrogenase and galactose oxidase are used and by which galactose and galactono-δ-lactone, or galactose and NADPH are assayed (pH of the buffer=about 8 to about 10).

Although ordinary solution reactions may be performed without immobilizing the enzymes, reaction time control is difficult and expensive dehydrogenases can be used only once in solution systems. Thus, solution systems are not suited for analyzing a large number of samples. In assay apparatus in which column-shaped reactors are disposed in a continuous flow, the reaction time depends only on the rate of flow of the buffer solution or, in other words, the time of contact between the sample and each immobilized enzyme. Therefore, such apparatus are advantageous in that the reaction time can be readily controlled by precisely controlling the rate of flow.

The principle of measurement applied to the present invention, which enables simultaneous assay of an oxidized-form substrate $B_{oxidized}$ and a reduced-form substrate $B_{reduced}$ or simultaneous assay of a reduced-form substrate $B_{reduced}$ and a reduced-form coenzyme $A_{reduced}$, is now explained in the following.

Figure 7:
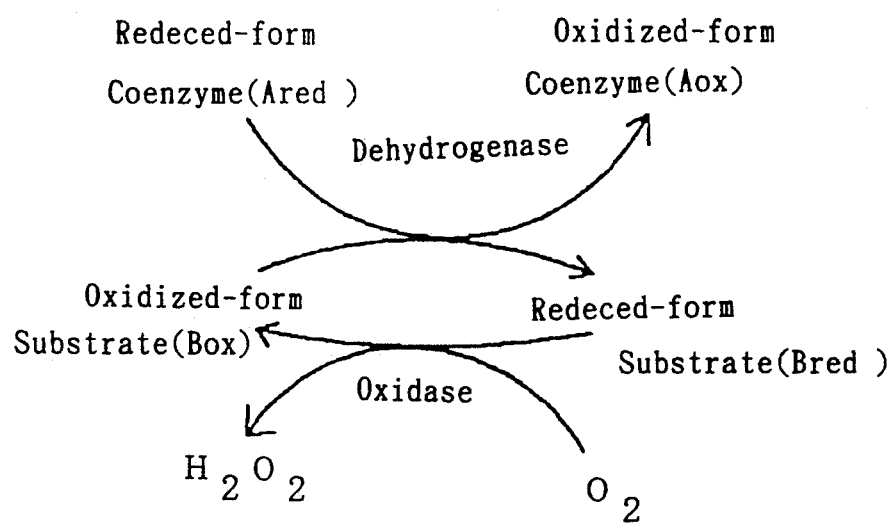
FIG. 7 is a schematic view showing the oxidase- and dehydrogenase-catalyzed reactions.

As shown in FIG. 7, the reactions involving a dehydrogenase and an oxidase proceed as follows:

Dehydrogenase:

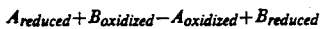

$$A_{reduced} + B_{oxidized} \rightarrow A_{oxidized} + B_{reduced}$$

Oxidase:

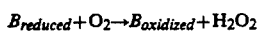

$$B_{reduced} + O_2 \rightarrow B_{oxidized} + H_2O_2$$

L-lactate dehydrogenase:

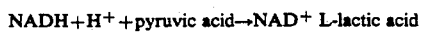

$$NADH + H^+ + \text{pyruvic acid} \rightarrow NAD^+ \text{ L-lactic acid}$$

L-lactate oxidase:

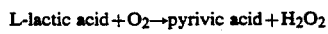

$$\text{L-lactic acid} + O_2 \rightarrow \text{pyruvic acid} + H_2O_2$$

First, to determine the concentration of the oxidized-form substrate $B_{oxidized}$ (or reduced-form coenzyme $A_{reduced}$) by means of the dehydrogenase-catalyzed reaction, a sufficient amount of the reduced-form coenzyme $A_{reduced}$ (or oxidized-form substrate $B_{oxidized}$) is added to a buffer which carries the sample, to thereby cause formation of the reduced-form substrate $B_{reduced}$. The reduced-form substrate $B_{reduced}$ then contacts with the immobilized oxidase to give the oxidized-form substrate $B_{oxidized}$ and an electrochemically active substance (e.g. hydrogen peroxide). The electrochemically active substance (for example, generated $H_2O_2$ or decreased $O_2$) which varies in concentration upon the oxidase-catalyzed reaction is then detected, whereby the oxidized-form substrate $B_{oxidized}$ (or reduced-form coenzyme $A_{reduced}$) can be assayed. However, this technique is applicable only when the sample is free from the reduced-form substrate $B_{reduced}$.

In case the sample contains the reduced-form substrate $B_{reduced}$ from the beginning, the concentration thereof additionally contributes to the assay result, namely the sum of the reduced-form substrate $B_{reduced}$ from the beginning and that concentration of $B_{reduced}$ resulting from the dehydrogenase-catalyzed reaction of the oxidized-form substrate $B_{oxidized}$ (or reduced-form coenzyme $A_{reduced}$) according to the above reaction equation is measured. It is thus impossible to determine the concentration of the oxidized-form substrate $B_{oxidized}$ (or reduced-form coenzyme $A_{reduced}$) alone.

Therefore, in accordance with the invention, the reduced-form substrate $B_{reduced}$ in a sample is independently assayed by means of the immobilized oxidase and then, the total amount of the oxidized-form substrate $B_{oxidized}$ (or reduced-form coenzyme $A_{reduced}$) and the reduced-form substrate $B_{reduced}$ is determined by the above-mentioned procedure. By doing so, the contribution of that reduced-form substrate $B_{reduced}$ occurring in the sample from the beginning is canceled for correction purposes, whereby the oxidized-form substrate $B_{oxidized}$ (or reduced-form coenzyme $A_{reduced}$) can be assayed correctly. Simultaneous assay of the two components in question thus becomes possible.

This simultaneous assay technique has made it possible to assay two components with very high sensitivity and rapidity.

The relationship between outputs of the reduced-form substrate $B_{reduced}$ and the oxidized-form $B_{oxidized}$ in the first measuring part and second measuring part are determined by using working curves which are prepared by injecting standard solutions having a predetermined concentration of the reduced-form substrate $B_{reduced}$ and the oxidized-form $B_{oxidized}$. With respect to the working curve of the reduced-form substrate $B_{reduced}$, two sets of outputs of the standard solution of the reduced-form substrate $B_{reduced}$ are obtained from a first measuring part and a second measuring part, respectively so that two working curves (No.1: a first measuring part, No.2: a second measuring part) are prepared. In contrast, with respect to the working curve of the oxidized-form substrate $B_{oxidized}$, one set of outputs of the standard solution of the oxidized-form substrate $B_{oxidized}$ is obtained from only the second measuring part so that one working curve No.3 is prepared. In total, three working curves are prepared.

An example of the assay apparatus of the invention are described below with reference to FIG. 1.

FIG. 1 discloses an example of a flow-type assay apparatus of the invention. The apparatus comprises:

(a) a first measuring part set an oxidase in immobilized form (4) and a first electrode (5) disposed downstream of the first measuring part, and (b) a second measuring part set a dehydrogenase in immobilized form (6), an oxidase in immobilized form (7) and a second electrode (8) which are disposed in this order from the upstream, the second measuring part being disposed in line with the first measuring part.

For assaying an oxidized-form substrate $B_{oxidized}$ and a reduced-form substrate $B_{reduced}$, for instance, the reduced-form substrate $B_{reduced}$ contained in the sample is first assayed by incorporating a value measured in the above-mentioned first measuring part into the working curve No.1.

Thus, the buffer solution containing the sample and the reduced-form coenzyme $A_{reduced}$ is fed to the first measuring part by means of a feed pump (2). The immobilized oxidase catalyzes the conversion of the reduced-form substrate $B_{reduced}$ to the oxidized-form substrate $B_{oxidized}$. The concentration of the electrochemically active substance formed on that occasion is measured by means of the first electrode (5), whereby the reduced-form substrate $B_{reduced}$ originally contained in the sample is assayed directly.

Then, in the second measuring part equipped with the immobilized dehydrogenase (6), the immobilized oxidase (7) and the second electrode (8) for detecting the change in the concentration of the electrochemically active substance as resulting from the final-step oxidase-catalyzed reaction, the total concentration of the reduced-form substrate $B_{reduced}$ formed from the oxidized-form substrate $B_{oxidized}$ contained in the sample and the reduced-form coenzyme $A_{reduced}$ by the dehydrogenase-catalyzed reaction and the reduced-form substrate $B_{reduced}$ contained in the sample from the beginning is detected. The oxidized-form substrate $B_{oxidized}$ in the sample can be quantitated by putting the concentration of the reduced-form substrate $B_{reduced}$ originally contained in the sample as determined previously in step (i) in place of the concentration of $B_{reduced}$ in the working curve No.2, and subtracting the obtained value from the output value of $B_{reduced}$ obtained in the second measuring part. And the subtracted output value is put into the working curve No.3 to obtain the concentration of $B_{oxidized}$. In this way, the reduced-form substrate $B_{reduced}$ and oxidized-form substrate $B_{oxidized}$ can be assayed simultaneously.

The step (iii) of correcting the value obtained in step (ii) in the light of the value obtained in step (i) can be automated by computer programming.

Taking, as an example, the case in which L-lactate dehydrogenase is used as the dehydrogenase and L-lactate oxidase as the oxidase, each in immobilized form, the conditions of measurement and other details are further explained below.

The method of immobilizing the dehydrogenase or oxidase is not limited to any particular one but may includes the adsorption method, chemical coupling or covalent binding method, entrapping method, and other methods per se known in the art. Among these, the chemical binding method by which firm enzyme immobilization can be attained is preferred, however. In a preferred mode of immobilization, enzymes are immobilized on a finely divided carrier and each immobilized enzyme is incorporated into a reactor, for example a column, in order to achieve improved sensitivity in the measurement.

As examples of the carrier to be used for immobilization, there may be mentioned diatomaceous earth, silica gel, glass beads, alumina, ceramic materials, carbon, activated carbon, molecular sieves, silicone rubbers, cellulose, agarose, amino acid-based polymers and the like. In a preferred example of the chemical coupling method, an amino group is introduced into the carrier surface by means of an aminosilane reagent and, after further treatment for formylation using a multifunctional aldehyde such as glutaraldehyde, an enzyme is brought into contact with the carrier for immobilization.

More specifically, a support having hydroxyl groups, such as diatomaceous earth, calcined diatomaceous earth (fire brick, etc.), cellulose, porous glass, silica gel or acid clay is treated for conversion of hydroxyl groups to aminosilane, and reacted with a polyfunctional aldehyde, whereby the polyfunctional aldehyde is covalently bonded to the amino groups formed on the surface of the support to introduce the aldehyde groups onto the support. Subsequently enzyme is bonded to the aldehyde groups for immobilization. Such immobilized dehydrogenase or oxidase is preferred in view of operational efficiency and less decrease of enzyme activity. Of these supports, preferred are diatomaceous earth, calcined diatomaceous earth, porous glass, silica gel, acid clay and the like which comprise silicate. More preferred are diatomaceous earth and calcined diatomaceous earth.

The conversion of hydroxyl groups to aminosilane can be done by bringing a reagent such as 3-aminopropyltriethoxysilane, 3-aminoethyltrimethoxysilane, or the like into contact with the support in a solvent such as anhydrous benzene, toluene or the like. Useful polyfunctional aldehydes include glutaraldehyde, glyoxal, succinyldialdehyde, etc.

First, L-lactate dehydrogenase or L-lactate oxidase, and like dehydrogenase or oxidase are each immobilized by the chemical binding method to give the corresponding immobilized enzymes each in finely divided form. The immobilized enzymes are respectively packed in plastic or stainless steel columns having an inside diameter of about 1 to 10 mm and a length of about 2 to 50 mm, to give respective reactors. The reactors may be different in size so that the assay concentration range can be varied.

Then, a pump is prepared which can feed 1 to 500 mM phosphate buffer with a pH of 7.0, as a buffer solution having a pH close to the optimum pH of said enzymes, at a flow rate of about 1.0 ml/minute. Usable as such pump are pumps of various types, such as the plunger type, peristaltic type and so on. The buffer solution mentioned above may contain another or other salts, a stabilizer, a surfactant and/or the like. The assay temperature is preferably about 25° to 35° C.

The sample-feeding mechanism may be, for example, an injector for high-performance liquid chromatography in which a 6-way valve is used. An immobilized oxidase-containing reactor is disposed downstreams of the injector and L-lactic acid in the sample is first oxidized in said reactor, whereupon as the electrochemically active substance the concentration of hydrogen peroxide increases and the concentration of oxygen decreases. Therefore, when a first hydrogen peroxide electrode or oxygen electrode is disposed downstreams of the immobilized oxidase-containing reactor, an output value corresponding to the amount of L-lactic acid can be obtained.

Further downstreams of said immobilized oxidase-containing reactor and electrode, an immobilized dehydrogenase-containing reactor and an immobilized oxidase-containing reactor are disposed in that order. Downstreams thereof, a second hydrogen peroxide electrode or oxygen electrode is disposed.

For assaying L-lactic acid and pyruvic acid, NADH is added to the buffer solution. The level of addition of NADH depends on the extent to which the sample introduced through the injector is diluted by blending with the buffer solution until it has reached the immobilized dehydrogenase-containing reactor. The reduction of pyruvic acid to L-lactic acid proceeds in an NADH-:pyruvic acid mole ratio of 1:1. Generally, the NADH concentration is sufficient if it is about one-half to about one hundredth of the concentration of pyruvic acid in the sample. Although it is also possible to add NADH to the sample and inject the resulting mixture into the assay apparatus through which the NADH-free buffer solution is flowing, this technique is not preferable from the cost viewpoint since NADH is diluted simultaneously with pyruvic acid, which is one of the assay targets, so that an increased amount of NADH is required at the solution volume level practical for handling.

For the sample injected, L-lactic acid is first assayed by means of the first reactor and first electrode. Then, the pyruvic acid formed from L-lactic acid and the pyruvic acid originally contained in the sample from the beginning are both reduced in the immobilized dehydrogenase-containing reactor. This reaction progresses at a high rate since the dehydro-genase reaction equilibrium is much more favorable for the formation of L-lactic acid.

The L-lactic acid formed from pyruvic acid by the action of the dehydrogenase is then oxidized under the action of the oxidase and thus can be quantitated based on the concentration-dependent output value of the hydrogen peroxide electrode or oxygen electrode. The relationship of the first and second electrode output values with the L-lactic acid concentration can be found by injecting, prior to assay of the sample, standard solutions of L-lactic acid. The relation between the second electrode output value and the pyruvic acid concentration can be found by injecting standard pyruvic acid solutions. As a result, two working curves are obtained for L-lactic acid and one working curve is obtained for pyruvic acid.

In the analysis of pyruvic acid and L-lactic acid mixtures, the concentration of L-lactic acid is first determined and the influence of L-lactic acid on the second electrode can be estimated. The concentration of pyruvic acid originally contained in the sample can be calculated by subtracting the contribution of the influence of L-lactic acid. These processings can be readily performed by transferring the two electrode outputs, after A/D conversion, to a microcomputer. For simultaneous assay of L-lactic acid and NADH, pyruvic acid is added to the buffer solution in lieu of NADH. The above series of procedures can be applied to other enzyme combinations. Even above series of procedures can be applied to other enzyme combinations. Even when an oxidized-form substrate and a reduced-form coenzyme coexist in the sample, the assay results are not affected thereby.

The electrode for detecting the change in the concentration of an electrochemically active substance is, for example, a hydrogen peroxide electrode or an oxygen electrode. Materials that can be used as the hydrogen peroxide electrode body are carbon, platinum, nickel, palladium, etc on the anode side. Platinum is preferred, because the overvoltage is low, a high sensitivity can be obtained and the potential window is broad. The electrode surface may have a selectively permeable membrane such as a polysiloxane, acrylic resin, protein or acetylcellulose membrane, etc. On the cathode side, carbon, gold, platinum, lead and the like can be used. The anode and cathode may be disposed in a cylinder which contains an internal solution containing an electrolyte such as potassium chloride, or the anode and cathode may be inserted into the stream of the buffer solution which contains an electrolyte such as potassium chloride. Furthermore, the three-electrode system comprising a working electrode, reference electrode and counter electrode may be employed. The oxygen electrode may of any type known in the art. Among these electrodes, the three-electrode type hydrogen peroxide electrode is desirable from the viewpoints of stability, response speed and accuracy. The electrode is generally set in the flow cell and constitutes a measuring part.

Figure 8:
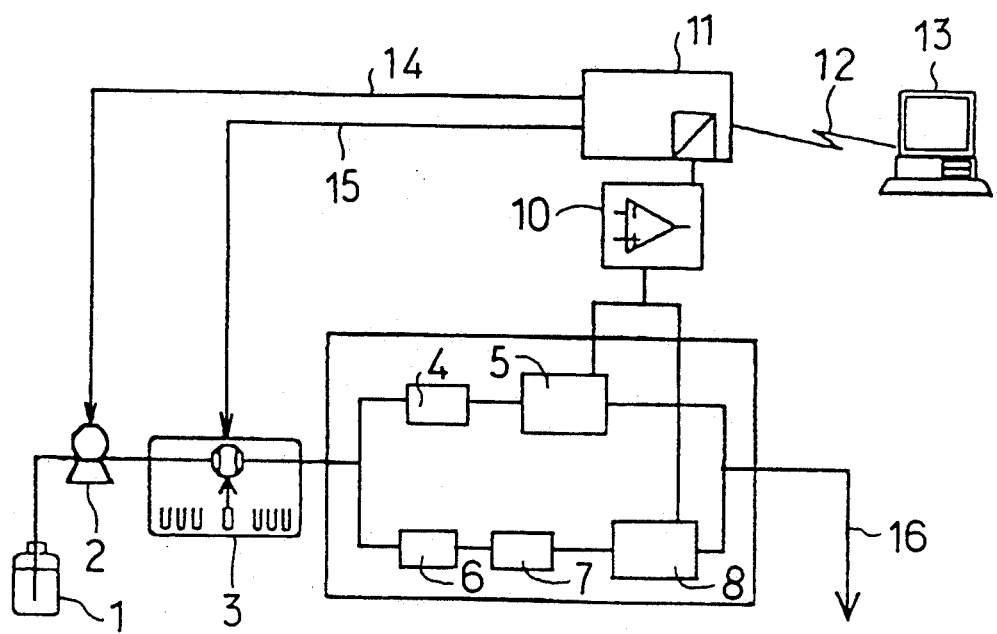
FIG. 8 shows an apparatus disposing a first measuring part and second measuring part in parallel.

FIG. 8 shows the apparatus as a different embodiment as shown in FIG. 1 comprising a first measuring part provided with an immobilized oxidase (4) and a first electrode (5), and a second measuring part provided with an immobilized dehydrogenase (6), an immobilized oxidase (4) and a second electrode (8), with said second measuring part disposed parallel to the first measuring part. Said first measuring part and second measuring part may be disposed in parallel instead of in series.

The embodiment of the invention as shown in FIG. 1 is more preferable than that of FIG. 8, since alteration of the separation ratio of a sample between a first measuring part and a second measuring part to cause decrease of accuracy of data may be occurred in the apparatus of FIG. 8.

Figure 9:
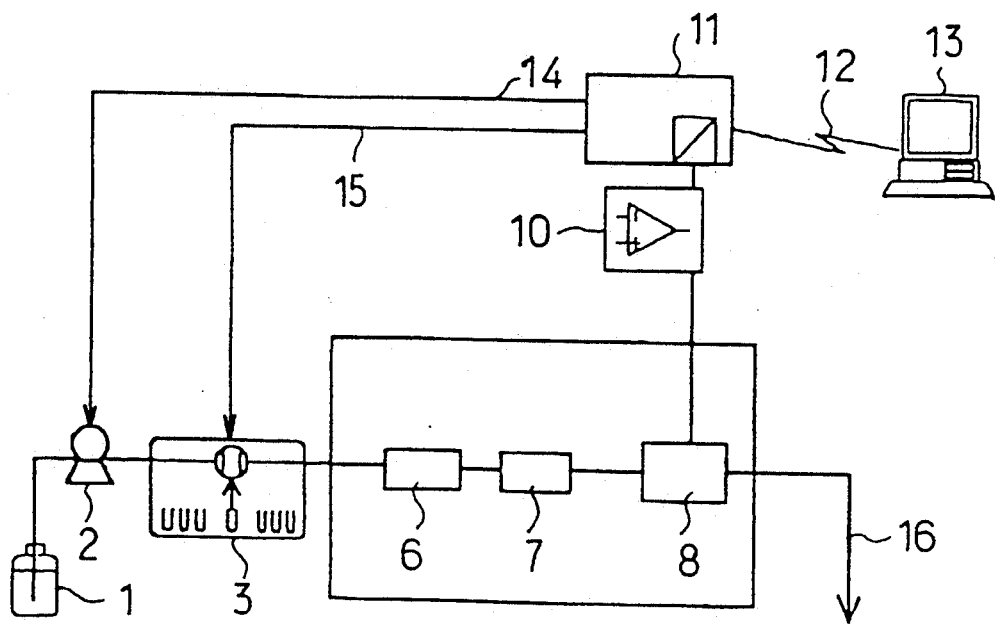
FIG. 9 show a flow-type apparatus of the invention.

In addition, the invention can be performed using a flow-type apparatus as shown in FIG. 9. The apparatus of FIG. 9 is different from the apparatus of FIG. 1. And the apparatus of FIG. 9 lacks a first measuring part provided with an immobilized oxidase (4) and a first electrode.

The step of measuring reduced-form substrate $B_{reduced}$ is performed in the same manner as the assay method mentioned above at a the first measuring part, by without using the reduced-form coenzyme $A_{reduced}$ in a buffer solution not to cause a dehydrogenase reaction. Then, the step of measuring the oxidized-form substrate $B_{oxidized}$ are assayed using a reduced-form coenzyme $A_{reduced}$ containing buffer solution in the same manner as an assay method at a second measuring part mentioned above regarding the apparatus shown in FIG. 1.

This method has a benefit without a necessity of using a more complicated apparatus shown in FIG. 1 or FIG. 8. On the other hand, the method has drawbacks in that sample injection is required twice and that in each case using buffer solutions containing and lacking the reduced-form coenzyme $A_{reduced}$ is necessary. Of course, reduced-form coenzyme $A_{reduced}$ can be added to a sample instead of the buffer solution.

The argument mentioned above is about the measurement of oxidized-form substrate $B_{oxidized}$ and the reduced-form substrate $B_{reduced}$. However, this argument can be applied to the measurement of the reduced-form coenzyme $A_{reduced}$ and the reduced-form substrate $B_{reduced}$.

The following examples illustrate the invention in further detail. Of course, they are by no means limitative of the scope of the invention.

EXAMPLE 1

Assay apparatus for L-lactate and pyruvate were constructed and the respective immobilized enzyme reactors were examined for their characteristics.

(1) PRODUCTION OF A REACTOR CONTAINING IMMOBILIZED L-LACTATE OXIDASE

A firebrick powder (diatomaceous earth-type siliceous carrier; 30–60 mesh; 150 mg) is thoroughly dried, immersed in a 10% solution of γ-aminopropyltriethoxysilane in anhydrous toluene for 1 hour, then thoroughly washed with toluene and dried at 120° C. for 2 hours. The aminosilane-modified carrier is immersed in a 5% aqueous glutaraldehyde solution for 1 hour and then thoroughly washed with distilled water, followed by substitution with 100 mM sodium phosphate buffer (pH 7.0). The buffer is removed as far as possible. A solution (200 μl) of L-lactate oxidase (Sigma Chemical Company) (50 units/ml) in 100 mM sodium phosphate buffer (pH 7.0) is brought into contact with the formylated firebrick. The mixture is allowed to stand at 10° C. or below for 1 day for enzyme immobilization. The thus-obtained immobilized enzyme-bearing carrier is packed into an acrylic resin column (3.5 mm in inside diameter, 30 mm in length) to give a reactor containing immobilized L-lactate oxidase.

(2) PRODUCTION OF A REACTOR CONTAINING IMMOBILIZED L-LACTATE DEHYDROGENASE

The same formylated firebrick as used for immobilizing L-lactate oxidase is contacted with 200 μl of a solution of swine muscle-derived L-lactate dehydrogenase (product of Boehringer Mannheim) (4,500 units/ml) in 100 mM sodium phosphate buffer (pH 7.0) and the mixture is allowed to stand at 10° C. or below for 1 day for enzyme immobilization. The thus-obtained immobilized enzyme-bearing carrier is packed into a column (3.5 mm in inside diameter, 30 mm in length) to give a reactor containing immobilized L-lactate dehydrogenase.

(3) PRODUCTION OF A HYDROGEN PEROXIDE ELECTRODE

The side face of a platinum wire with a diameter of 2 mm is covered with heat-shrinking Teflon and one end of the wire is smoothed using a file and #1500 emery paper. Using this wire as a working electrode, a platinum plate (1 cm×1 cm) as a counter electrode and a saturated calomel electrode as a reference electrode, electrolytic treatment of working electrode is performed in 0.1 M sulfuric acid at +1.4 V for 10 minutes. The platinum wire is then thoroughly washed with water, dried at 40° C. for 10 minutes, immersed in a 10% solution of γ-aminopropyltriethoxysilane in anhydrous toluene for 1 hour and then washed. Glutaraldehyde is added to a solution of 20 mg of bovine serum albumin (product of Sigma Chemical Co., Fraction V) in 1 ml of distilled water to a glutaraldehyde concentration of 0.2%. A 5-μl portion of the resulting mixture is quickly placed on the platinum wire prepared as mentioned above, followed by drying and curing at 40° C. for 15 minutes, whereby a membrane selectively permeable to hydrogen peroxide is formed. The platinum wire thus processed is used as the working electrode of a hydrogen peroxide electrode.

A silver-silver chloride electrode is used as a reference electrode and mounted on a flow cell. On the flow cell outlet side, a conductive piping is used as a counter electrode. For detecting hydrogen peroxide, an voltage of +0.6 V relative to the silver-silver chloride reference electrode is applied to the working electrode.

(4) APPARATUS FOR SIMULTANEOUS ASSAY OF L-LACTIC ACID AND PYRUVIC ACID

FIG. 1 is referred to. A buffer solution containing 0.5 mM NADH is continuously fed from a buffer tank (1) by a feed pump (2) and carries a sample containing pyruvic acid and L-lactic acid as injected via a sampler (3) toward a constant-temperature vessel (9). In a first immobilized L-lactate oxidase (4)-containing reactor in said vessel, pyruvic acid and hydrogen peroxide are formed from L-lactic acid in the sample and oxygen in the buffer solution. This change is detected in a first measuring part (5) equipped with a first hydrogen peroxide electrode.

The portion of pyruvic acid originally contained in the sample and the portion of pyruvic acid formed by the L-lactate oxidase-catalyzed reaction further react with NADH in the buffer solution in a reactor containing immobilized L-lactate dehydrogenase (6) to give L-lactic acid and NAD. Then, in a second immobilized L-lactate oxidase (7)-containing reactor, hydrogen peroxide is formed in the same manner as mentioned above. This change is detected at a measuring part (8) equipped with a second hydrogen peroxide electrode. The changes in electric current in these two measuring parts are converted to voltages by a detector (10), for example a potentiostat, and the voltages, after further A/D conversion, are sent to a single board computer (11) The voltage data are finally sent to a personal computer (13) via an RS-232C cable (12) for data processing. The sample injection and pump control are conducted by means of a personal computer. In FIG. 1, the reference number (14) indicates a pump control signal, (15) a sampler control signal and (16) a waste liquid.

(5) ASSAY METHOD

The above-mentioned assay apparatus for L-lactic acid and pyruvic acid is used. The amount of the sample injection is 5 μl. In a blank test, water is used. Standard L-lactic acid solutions (1.0 mM and 2.5 mM; prepared by dissolving lithium L-lactate in distilled water) and standard pyruvic acid solutions (1.0 mM, 2.5 mM and 5.0 mM; prepared by dissolving lithium pyruvate in distilled water) are assayed. The working curve of L-lactic acid and pyruvic acid are constructed.

The composition of the buffer solution is s follows: 100 mM phosphoric acid, 50 mM potassium chloride, 1 mM sodium azide and 500 μM NADH. The measurements are made at pH 7.0 and at a buffer solution flow rate of 1.0 ml/minute. The temperature of the vessel is 30° C.

Figure 2:
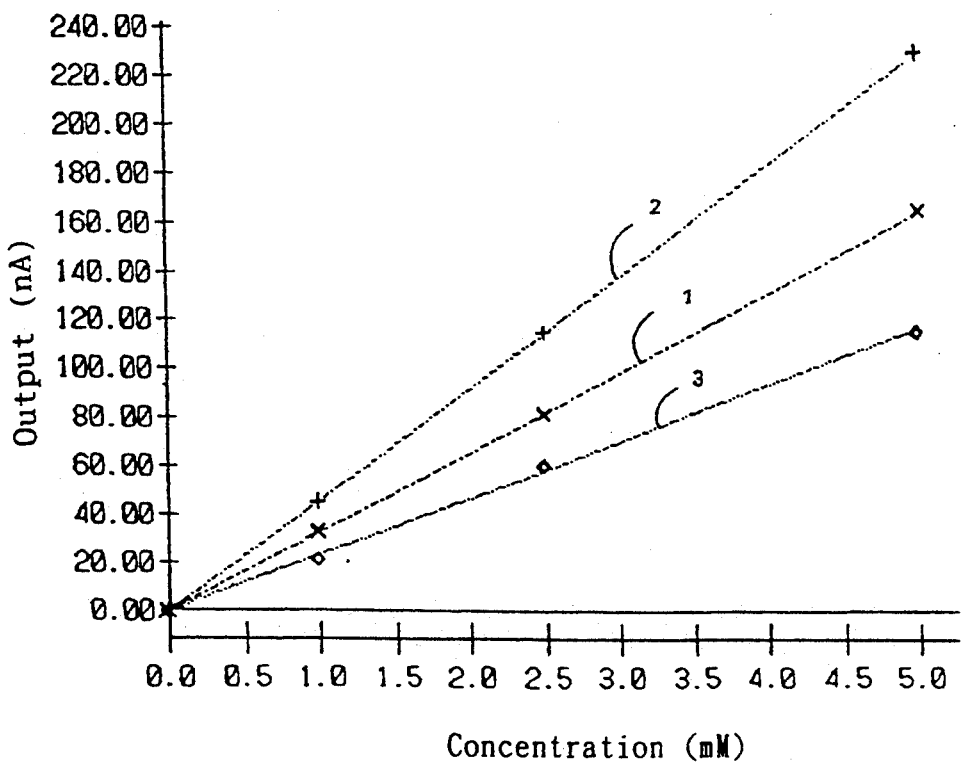
FIG. 2 shows the results of working curve construction for L-lactic acid (output from a first measuring part; line 1), L-lactic acid (output from a second measuring part; line 2) and pyruvic acid (line 3), at pH 7.0.

The working curves constructed based on the output values obtained from the two measuring parts at pH 7.0 are shown in FIG. 2. Working curve 1 is for the output for lactic acid from the first measuring part, working curve 2 for the output for lactic acid from the second measuring part and working curve 3 for the output for pyruvic acid. Good linearity is evident for each working curve.

Figure 3:
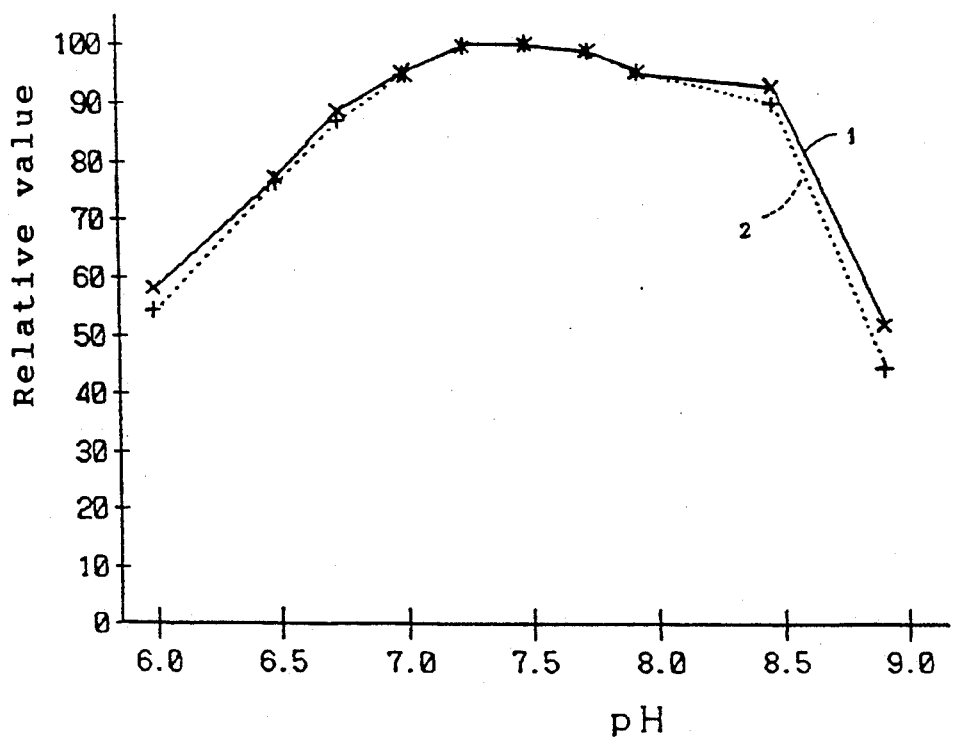
FIG. 3 shows the relative values of lactic acid (1) and pyruvic acid (2) at various pH levels.

Working curves were constructed in the same manner as above except that the pH of the buffer solution was varied. The variations from the output values at pH 7.0 were examined based on the gradients of the curves. The results are shown in FIG. 3. Curve 1 in the figure shows pH dependency of the response value for lactic acid. When expressed in terms of relative values, the output values for lactic acid from the first and second measuring parts showed the same behavior, hence the behavior is represented by one curve. Curve 2 is for the output value for pyruvic acid. A maximum is observed approximately at pH 7.25.

Figure 4:
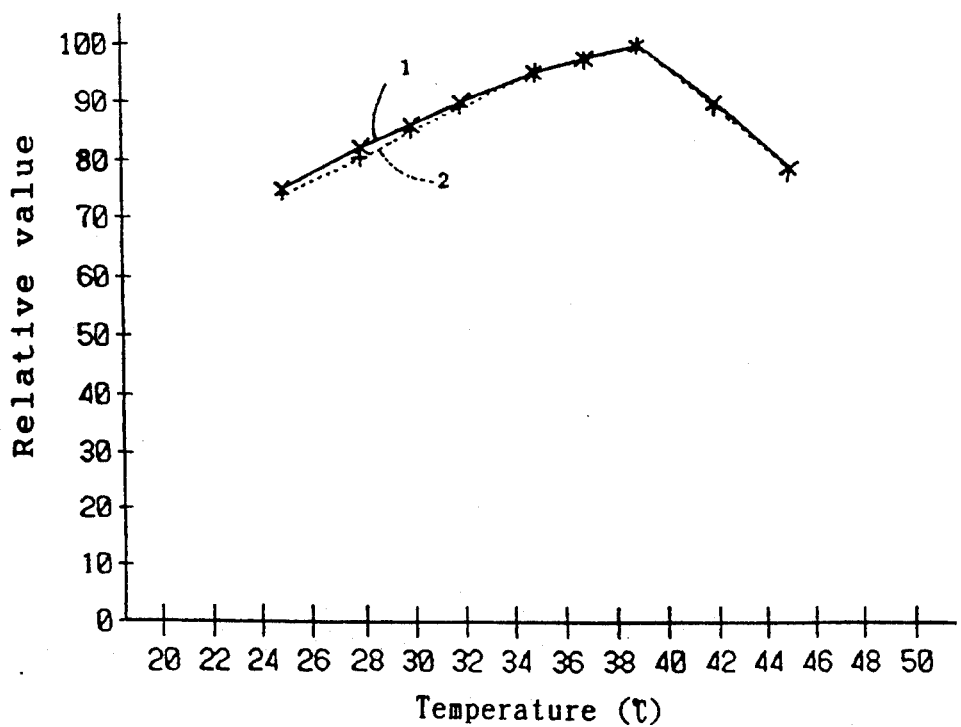
FIG. 4 shows the relative values of lactic acid (1) and pyruvic acid (2) at various temperature levels.

Further, the temperature of the vessel was varied and the changes in gradient were expressed in terms of relative values. The results are shown in FIG. 4. As in FIG. 3, only one curve is shown for the changes in response value for lactic acid. Curve 2 shows the changes in response value for pyruvic acid in the measuring part equipped with the second electrode. An optimal temperature is observed at about 39° C.

The time required for each assay run is 90 seconds, hence rapid assay is possible.

Figure 5:
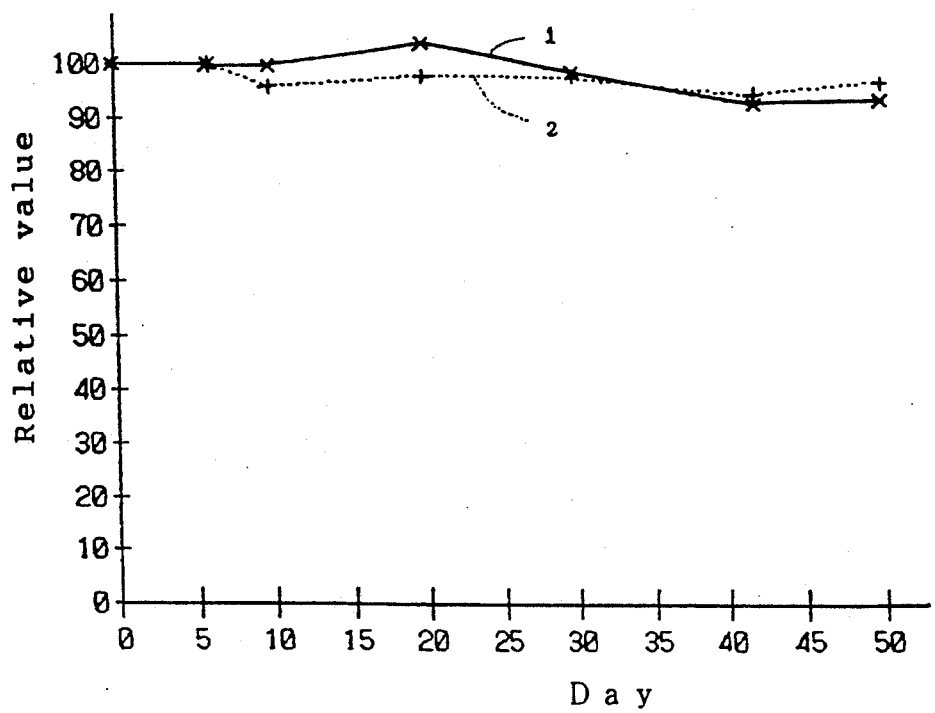
FIG. 5 shows between-day variations of the assay values for L-lactic acid (1) and pyruvic acid (2).

Based on the results of the above experiments, the pH of 7.0 and the temperature 30° C. were selected. Using the above assay apparatus, assay was repeated at 30° C. for 8 hours every day and the immobilized enzymes were allowed to stand at room temperature (25° C.) for the rest of each day, for long-term stability evaluation. The between-day variations are shown in FIG. 5, with the output value immediately after immobilization being expressed as 100. In FIG. 5, curve 1 is concerned with lactic acid and curve 2 with pyruvic acid. It was found that the enzymes are stable over a period of about 2 months.

EXAMPLE 2

Standard mixed solutions of L-lactic acid and pyruvic acid, and sake moromi (sake mash) filtrate samples were analyzed.

(1) PRODUCTION OF IMMOBILIZED ENZYME-CONTAINING REACTORS

The same procedures as used in Example 1 were used for both the dehydrogenase and oxidase, respectively.

(2) PRODUCTION OF A HYDROGEN PEROXIDE ELECTRODE

The same procedure as used in Example 1 was used.

(3) ASSAY APPARATUS

The same assay apparatus as used in Example 1 was used.

(4) ASSAY METHOD

Assaying was carried out in the same manner as in Example 1. The pH of the buffer solution was 7.0 and the measurement temperature was 30° C.

The concentrations of the standard mixed solutions were as shown in Table 1.

(5) ASSAY RESULTS

The assay results for the standard mixed solutions are shown in Table 1.

TABLE 1

| Sample concentration (mM) | | Detected value (nA) | | Assayed value (mM) | |
|---|---|---|---|---|---|
| L-Lactic acid | Pyruvic acid | First cell | Second cell | L-Lactic acid | Pyruvic acid |
| 2.5 | 0.5 | 81 | 126 | 2.48 | 0.51 |
| 2.5 | 1.25 | 81 | 144 | 2.49 | 1.26 |
| 2.5 | 2.5 | 81 | 173 | 2.48 | 2.53 |
| 0.5 | 2.5 | 17 | 80 | 0.51 | 2.43 |
| 1.25 | 2.5 | 41 | 115 | 1.28 | 2.45 |
| 2.5 | 2.5 | 81 | 171 | 2.47 | 2.47 |

The working curve for L-lactic acid to be assayed at the first electrode in the first measuring part (5) gave the following equation:

$$Y = 32.6X + 0.13 \text{ (correlation coefficient: 1.000)}$$

where
X = L-lactic acid concentration (mM) and
Y = change in electric current (nA).

The working curve for L-lactic acid to be assayed at the second electrode in the second measuring part (8) gave the following equation:

$$Y = 46.2X - 0.31 \text{ (correlation coefficient: 1.000)}$$

where
X = L-lactic acid concentration (mM) and
Y = change in electric current (nA).

The working curve for pyruvic acid to be assayed at the second electrode gave the following equation:

$$Y = 23.4X + 0.03 \text{ (correlation coefficient: 0.999)}$$

where
X = pyruvic acid concentration (mM) and
Y = change in electric current (nA).

The L-lactic acid and pyruvic acid concentrations determined by using these working curves are correct, as shown above.

Sake moromi filtrates whose lactic acid and pyruvic acid contents had been determined by the dissolved enzyme method were analyzed by the present method without dilution. The results obtained are shown in Table 2.

TABLE 2

|  | Enzyme solution method | | Example 2 | |
| --- | --- | --- | --- | --- |
|  | L-Lactic acid | Pyruvic acid | L-Lactic acid | Pyruvic acid |
| Sample 1 | 1.0 mM | 2.3 mM | 0.98 mM | 2.28 mM |
| Sample 2 | 1.9 mM | 2.5 mM | 1.93 mM | 2.45 mM |
| Sample 3 | 5.1 mM | 3.8 mM | 5.15 mM | 3.82 mM |

As shown in Table 2, good agreement is found with the results of the dissolved enzyme method. The assay apparatus and assay method of the invention are thus advantageous in view of the fact that such an operation as dilution is unnecessary and in view of the possibility of automation of the analytical process.

EXAMPLE 3

Standard solutions containing L-lactic acid and NADH were analyzed.

(1) PRODUCTION OF IMMOBILIZED ENZYME-CONTAINING REACTORS

The same procedures as used in Example 1 were followed for the dehydrogenase and oxidase, respectively.

(2) PREPARATION OF A HYDROGEN PEROXIDE ELECTRODE

The same procedure as used in Example 1 was followed.

(3) ASSAY APPARATUS

The same assay apparatus as used in Example 1 was used.

(4) ASSAY METHOD

The method used in Example 2 was followed except that the buffer solution contained 0.5 mM pyruvic acid in lieu of NADH.

(5) ASSAY RESULTS

Figure 6:
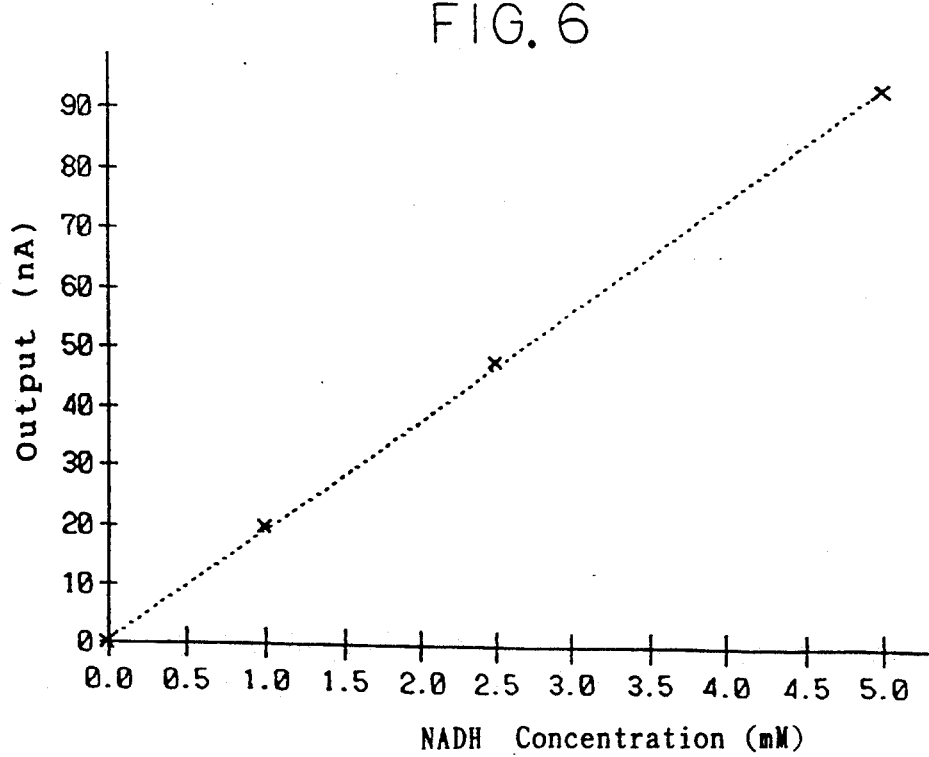
FIG. 6 shows the results of working curve construction for NADH.

For lactic acid, the results were the same as those obtained in Example 1. The working curve for NADH is shown in FIG. 6. It was revealed that NADH can be assayed using the apparatus and method of the invention. The results of analysis of the mixed solutions are shown in Table 3.

TABLE 3

| Sample concentration (mM) | | Assayed value (mM) | |
| --- | --- | --- | --- |
| L-Lactic acid | NADH | L-Lactic acid | NADH |
| 2.5 | 0.5 | 2.52 | 0.53 |
| 2.5 | 1.25 | 2.49 | 1.25 |
| 2.5 | 2.5 | 2.50 | 2.51 |
| 0.5 | 2.5 | 0.50 | 2.42 |
| 1.25 | 2.5 | 1.26 | 2.48 |
| 2.5 | 2.5 | 2.50 | 2.51 |

What is claimed is:

1. An apparatus for assaying either an oxidized-form substrate $B_{oxidized}$ or a reduced-form coenzyme $A_{reduced}$, and a reduced-form substrate $B_{reduced}$ by means of:

a dehydrogenase catalyzing the reaction between the reduced-form coenzyme $A_{reduced}$ and oxidized-form substrate $B_{oxidized}$ to form the corresponding oxidized-form coenzyme $A_{oxidized}$ and reduced-form substrate $B_{reduced}$, and an oxidase catalyzing the oxidation of the reduced-form substrate $B_{reduced}$;

which apparatus comprises:

(1) a first measuring part including the oxidase in immobilized form and a first electrode for detecting the change in the concentration of an electrochemically active substance as resulting from the oxidiase-catalyzed reaction and (2) a second measuring part including the dehydrogenase in immobilized form and the oxidase in immobilized form and a second electrode for detecting the change in the concentration of an electrochemically active substance as resulting from the oxidase-catalyzed reaction.

2. The apparatus of claim 1, wherein the first and second measuring parts are connected in series, with the second measuring part disposed downstreams of the first measuring part and wherein, in the second measuring part, the dehydrogenase and oxidase are separately immobilized in respective reactors.

3. The assay apparatus of claim 1, wherein the dehydrogenase is L-lactate dehydrogenase and the oxidase is L-lactate oxidase.

4. The apparatus of claim 1 wherein dehydrogenase is immobilized in a reactor, and wherein said immobilized dehydrogenase is prepared by bonding an aminosilane coupling agent to a support having hydroxyl groups, then reacting the amino groups formed on the surface of the support with a polyfunctional aldehyde to bond the polyfunctional aldehyde thereto, and bonding dehydrogenase to the polyfunctional aldehyde.

* * * * *